US00PP27542P2

(12) United States Plant Patent
Kordes

(10) Patent No.: US PP27,542 P2
(45) Date of Patent: Jan. 17, 2017

(54) MINIATURE ROSE PLANT NAMED 'KORPOT048'

(50) Latin Name: *Rosa hybrida*
Varietal Denomination: KORpot048

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes Sohne Rosenschulen GMBH & CO. KG, Offenseth-Sparrieshoop (DE)

( * ) Notice: Subject to any disclaimer, the term of this patent is extended or adjusted under 35 U.S.C. 154(b) by 174 days.

(21) Appl. No.: 14/121,043

(22) Filed: Jul. 23, 2014

(51) Int. Cl.
*A01H 5/02* (2006.01)

(52) U.S. Cl.
USPC ..... Plt./118

(58) Field of Classification Search
USPC ..... Plt./118
See application file for complete search history.

*Primary Examiner* — Keith Robinson

(57) ABSTRACT

A new and distinct variety of rose with long lasting, novel yellow flowers with pink edges, and attractive foliage. It exhibits a compact upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida*.

Variety denomination: The denomination of the new variety is 'KORpot048'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2010 at the nursery of the breeder in Klein Offenseth-Sparrieshoop, Germany. The crossing was between an unnamed seedling, the seed parent, and an unnamed seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpot048'.

SUMMARY OF THE INVENTION

The new rose plant may be distinguished from its seed parent, an unnamed seedling, by the following combination of characteristics:

1. 'KORpot048' has yellow blooms with pink edges, whereas the unnamed seedling has orange blooms.
2. 'KORpot048' has a flat flower shape, whereas the unnamed seedling has a round flower shape.

The new rose plant may be distinguished from its pollen parent, an unnamed seedling, by the following combination of characteristics:

1. 'KORpot048' has an above average shelf life, whereas the unnamed seedling has an average shelf life.
2. 'KORpot048' has a flat flower shape, whereas the unnamed seedling has a pointed flower shape.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers and foliage;
3. Resistance to diseases encountered in greenhouse and nursery culture; and
4. Suitability for production from softwood cuttings in floral and nursery containers.

This combination of qualities is not present in prior rose cultivars known to the inventor. These objectives have been substantially achieved and in that distinguish 'KORpot048' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpot048' was selected in April 2011 from the seedling beds to be asexually propagated for further evaluation. The first asexual propagation of 'KORpot048' was done by rooting softwood cuttings in June 2011 at the inventor's nursery in Offenseth-Sparrieshoop, Germany.

These initial and other subsequent propagations conducted in controlled environments demonstrate that 'KORpot048' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot048' on a plant of 6 months of age.

DETAILED BOTANICAL DESCRIPTION

The following is a description of 'KORpot048', as observed growing in May 2014 in a nursery in Jackson County, Oreg. on plants of 6 months of age. Color references are made using The Royal Horticultural Society (London, England) Colour Chart, 2001 except where common terms of color are used.

For a comparison, several physical characteristics of the rose variety 'KORpot007', a rose variety from the same inventor described and illustrated in U.S. Plant Pat. No. 23,793 and issued on Aug. 6, 2013 are compared to 'KORpot048' in Chart 1.

CHART 1

| Characteristic | 'KORpot048' | 'KORpot007' |
|---|---|---|
| Bud Color as sepals unfold. | Red Group 45D. | Yellow Group 14D with petal margin Red Group 45B. |
| Petal Count. | Very Double 40-50 petals. | Double 38-40 petals. |
| Petal Reflex. | Petals reflex slightly. | Petals reflex strongly. |

Parents:

*Seed parent*.—An unnamed seedling.

*Pollen parent*.—An unnamed seedling.

Classification:

*Botanical classification*.—*Rosa hybrida* 'KORpot048'.

*Commercial classification*.—Miniature rose.

FLOWER AND FLOWER BUD

Blooming habit: Recurrent. Floriferous.

Flower bud:

*Size*.—Upon opening, 22 mm in length from base of receptacle to distal end of bud and 17 mm diameter at its widest point.

*Bud form*.—Globular.

*Bud color*.—As sepals first unfold, bud color is Red Group 45D. When ¼ open, the upper surface of the petals is Yellow Group 9C in the basal and middle zones, and Red Group 47C to 47B in the marginal zones. The lower surface is Yellow Group 9C with strong intonations of Red Group 47B in the middle and marginal zones. Guard Petals with intonations of Green-Yellow Group 1C and Grey-Yellow Group 160C in the basal zone and Red Group 53C in the middle and marginal zones.

*Sepals*.—Color: Upper surface is Yellow-Green Group 147B. Lower surface is Yellow-Green Group 146A. Size: Average 25-28 mm (l)×7 mm (w). Shape: Strong foliaceous appendages on 3 of the five sepals. Apex: Apiculate. Base: Flat at union with receptacle. Quantity: Five. Surface texture: Upper side: Pubescent. Lower surface: Smooth. Margins: Lightly pubescent with limited numbers of stipitate glands.

Flower bloom:

*Fragrance*.—None.

*Duration*.—On the plant 14 to 17 days. Senesced petals somewhat clinging.

*Size*.—Medium for a miniature rose. When open, the average flower diameter is 45 to 50 mm and the average flower height is 20 mm.

*Form*.—Shape of flower when viewed from the side: Upon opening, upper part: Flat. Upon opening, lower part: Flattened convex. Open flower, upper part: Flat. Open flower, lower part: Flattened convex.

Color:

*Upon opening, petals*.—Outermost petals: Outer Side: Yellow Group 4C with intonations of Red Group 46C. Inner Side: Yellow Group 3B in the basal and middle zones, and Red Group 47C and 47B in the marginal zone. Innermost petals: Outer Side: Yellow Group 7B with light intonations of Red Group 47B in the middle and marginal zones. Inner Side: Yellow Group 9A in the basal zone and Yellow Group 14A in the middle and marginal zones.

*Upon opening, basal petal spots*.—No distinctive coloration at petal base observed.

*After opening, petals*.—Outermost petals: Outer Side: Green-Yellow Group 1C with strong intonations of Red Group 47B in the middle and marginal zones. Inner Side: Yellow Group 3A with strong intonations of Red Group 47C and 47D in the middle and marginal zones. Innermost petals: Outer Side: Yellow Group 12B with light intonations of Red Group 47C in the marginal zones. Inner Side: Yellow Group 13A with intonations of of Red Group 47C in the marginal zone.

*After opening, basal petal spots*.—No distinctive coloration at petal base observed.

General tonality: On open flower Yellow-Orange Group 21A. No change in the general tonality at the end of the 6th day. Afterwards, general tonality is Yellow-Orange Group 16D.

Petals:

*Petal type*.—Very Double.

*Petal count*.—Approximately 40-50 petals under normal conditions.

*Petal reflex*.—Petals reflex slightly.

*Petal margin*.—Innermost petals: Entire. Outermost petals: Repand.

*Petal shape*.—Obovate. Apex: Obtuse. Base: Obtuse.

*Petal size*.—7 to 13 mm (l)×4 to 7 mm (w).

*Petal arrangement*.—Formal.

*Texture*.—Smooth.

Petaloids:

*Petaloid count*.—Average of 8 to 12 per flower.

*Petaloid size*.—7 to 13 mm (l)×4 to 7 mm (w).

*Petaloid color*.—Inner side: Yellow Group 13A. Outer side: Yellow Group 13A.

*Petaloid texture*.—Smooth.

*Margins*.—Undulated.

*Petaloid shape*.—Most commonly ovate to elliptical. Apex: Obtuse. Base: Cuneate.

Reproductive organs:

*Pistils*.—Abundant. Approximately 60 present. Stigmas: Location: Superior in position to anthers. Color: Green-Yellow Group 1C. Styles: Length: About 10 to 13 mm long. Color: Yellow-Green Group 148D.

*Stamens*.—Approximately 60 on average and regularly arranged. Anthers: Size: Average 2 mm (l)×1 mm (w). Pollen: Generally absent. Color: Yellow Group 13C. Filaments: Color: Green-Yellow Group 1B. Length: 4 mm.

*Ovary*.—Color White Group 155B.

*Receptacle*.—Surface: Smooth. Color: Yellow Group 144A. Shape: Urn-shaped. Texture: Smooth. Size: 8 mm (h)×7 mm (w).

*Pedicel*.—Surface: With fine hairs. Length: 25 to 28 mm average length. Diameter: 1.5 to 2 mm average diameter. Color: Yellow-Green Group 146B. Strength: Strong. Texture: Smooth.

*Peduncle*.—Surface: Glabrous, lacking fine hairs or stipitate glands. Length: 20 to 35 mm average length. Diameter: 2 to 3 mm average diameter. Color: Yellow-Green Group 146A with intonations of Greyed-Purple Group 183C. Strength: Strong. Borne: Multiple flower buds per stem, generally 5 to 7, occasionally borne singly. Flowers held upright.

*Inflorescence*.—Type: Panicle. Average Number of Flowers: Typically, 4-6 flowers. Average Size: 7 cm (h)×7 cm (w).

THE PLANT

Growth: Moderately vigorous.

Plant habit: Compact. Upright to bushy. When grown as a 10 cm pot plant, the average plant height is 20 cm and the average plant width is 11 cm.

Stems:

*Stem color*.—Young wood: Yellow-Green Group 146B. Older wood: Yellow-Green Group 146A.

*Intonations*.—Greyed-Purple Group 187C.

*Stem surface texture*.—Young wood: Smooth. Older wood: Smooth.

Prickles: Present. Sparse.

*Incidence*.—Average of 8 to 10 per each 10 cm of stem.

*Size*.—Average length: 4 to 5 mm.

*Color*.—Immature prickles: Greyed Red Group 181C. Mature prickles: Greyed Red Group 182A.

*Shape*.—Linear to concave.

*Texture*.—Smooth.

Leaves: Normally 5 leaflets on normal leaves in middle of the stem.

*Venation pattern*.—Pyramidal net pattern.

*Leaf size*.—85 to 90 mm (l)×75 mm (w).

*Abundance*.—Average.

Leaflets:

*Size*.—Average size of the terminal leaflet is 40 to 45 mm (l)×23.

*Shape*.—Base: Obtuse. Apex: Cuspidate.

*Margins*.—Finely serrated.

*Surface*.—Upper side of leaflet: Semi-glossy. Under side of leaflet: Semi-glossy.

*Shape*.—Ovate.

*Texture*.—Upper side of leaflet: Smooth. Under side of leaflet: Smooth.

*Color, mature foliage*.—Upper Leaflet Surface: Yellow-Green Group 147A. Lower Leaflet Surface: Yellow-Green Group 147B.

*Color, juvenile foliage*.—Upper Leaflet Surface: Yellow-Green Group 146A. Lower Leaflet Surface: Yellow-Green Group 146B.

*Arrangement*.—Odd pinnate.

*Venation*.—Reticulate.

Stipules:

*Size*.—12 to 15 mm (l)×5 mm (w).

*Stipule color*.—Yellow-Green Group 146A.

*Anthocyanin*.—Greyed Red Group 182C. Location: Upper side of midrib.

*Stipitate glands*.—Limited number on margins.

*Margins*.—Reflexed with stipitate glands present.

*Texture*.—Smooth.

*Shape*.—Apex: Apiculate. Base: Flat.

Petiole:

*Length*.—Average 12 mm.

*Diameter*.—Average 1 mm.

*Petiole color*.—Yellow-Green Group 146B. Underneath: Yellow-Green Group 146B.

*Margins*.—With stipitate glands.

*Anthocyanin*.—Greyed-Purple Group 187B.

*Prickles*.—No.

*Stipitate glands*.—Limited.

*Texture*.—Glabrous.

Petiole rachis:

*Length*.—Average 15 mm.

*Diameter*.—Average 1 mm.

*Color*.—Yellow-Green Group 146B. Anthocyanin: Greyed-Purple Group 187B.

*Margins*.—With stipitate glands.

*Prickles*.—A few small prickles underneath.

*Stipitate glands*.—Limited numbers of stipitate glands on margins.

Roots:

*Type*.—Fibrous.

*Habit*.—Freely branched both shallow and deep.

Hips/seed formation: None observed.

Winter hardiness: To date, the variety has been grown successfully in Zones 7-8.

Disease resistance: Above average resistance to Powdery mildew (*Sphaerotheca pannosa*), and *Botrytis* (*Botrytis cinerea*) diseases under normal growing conditions in Jackson County, Oreg.

I claim:

1. A new and distinct variety of rose plant, as described and illustrated herein.

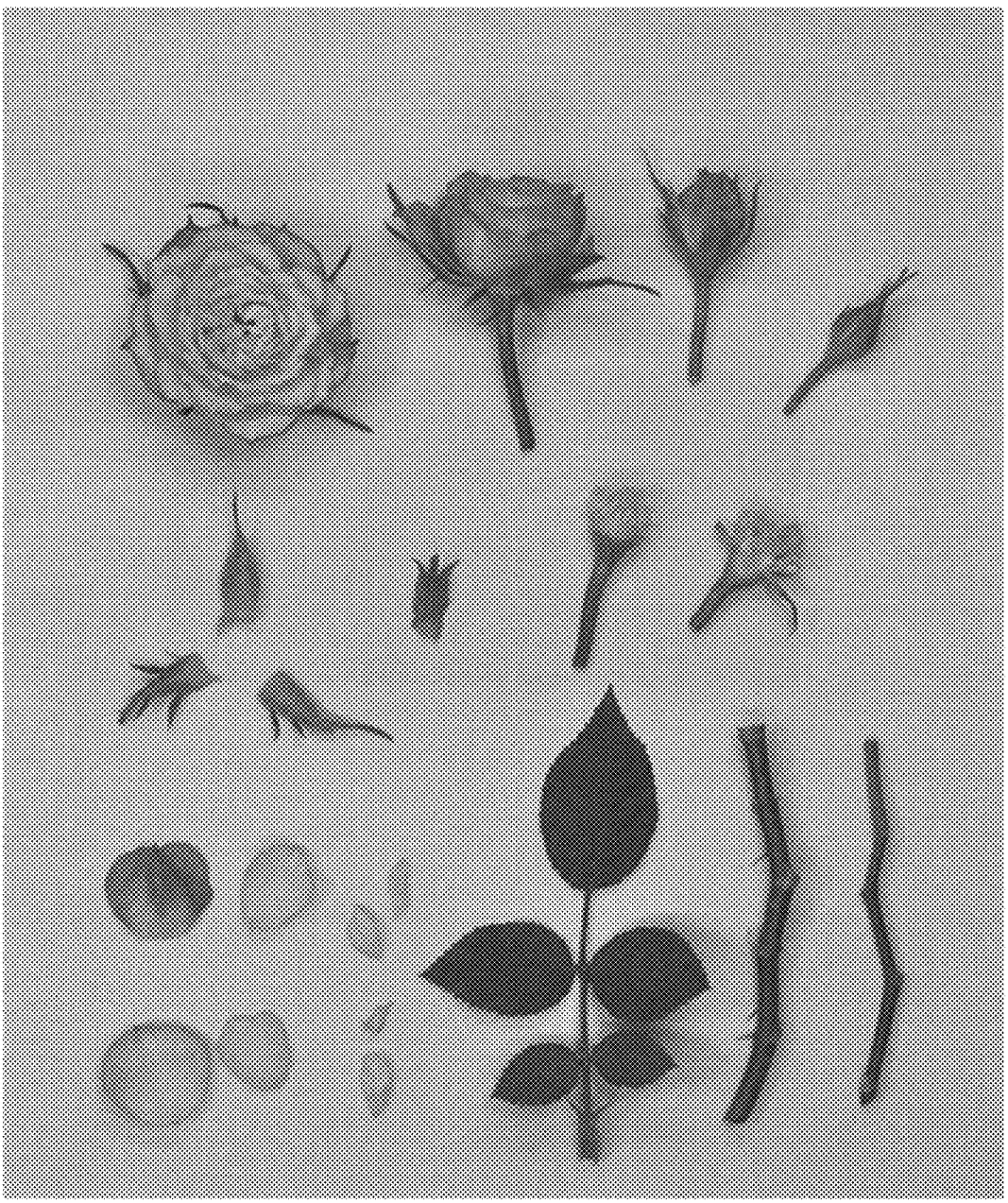

* * * * *